(12) United States Patent
Puhalla et al.

(10) Patent No.: US 10,444,176 B2
(45) Date of Patent: Oct. 15, 2019

(54) SENSING SYSTEM FOR MEASURING SOIL PROPERTIES IN REAL TIME

(71) Applicant: Deere & Company, Moline, IL (US)

(72) Inventors: Jeffrey S. Puhalla, Hawley, MN (US); Michael Rhodes, Richfield, MN (US); Nikolai Tevs, Daytona Beach Shores, FL (US); Kartheek Karna, Fargo, ND (US); Noel W. Anderson, Fargo, ND (US)

(73) Assignee: DEERE & COMPANY, Moline, IL (US)

( * ) Notice: Subject to any disclaimer, the term of this patent is extended or adjusted under 35 U.S.C. 154(b) by 387 days.

(21) Appl. No.: 15/436,185

(22) Filed: Feb. 17, 2017

(65) Prior Publication Data

US 2018/0238823 A1    Aug. 23, 2018

(51) Int. Cl.
*G01N 27/22* (2006.01)
*G01N 33/24* (2006.01)
(Continued)

(52) U.S. Cl.
CPC .......... *G01N 27/223* (2013.01); *A01B 47/00* (2013.01); *A01C 21/007* (2013.01); *G01N 27/221* (2013.01); *G01N 33/246* (2013.01); *G01S 19/13* (2013.01); *A01B 79/005* (2013.01); *A01C 5/064* (2013.01); *G01N 2033/245* (2013.01)

(58) Field of Classification Search
CPC ...... G01N 27/22; G01N 33/24; G01N 33/246; G01N 2033/243; G01N 2033/245; G01R 27/26; G01S 19/13; A01C 21/007; A01C 5/046; A01B 47/00; A01B 79/005
See application file for complete search history.

(56) References Cited

U.S. PATENT DOCUMENTS

| | | | |
|---|---|---|---|
| 6,484,652 B1 | 11/2002 | Colburn | |
| 8,807,910 B1 | 8/2014 | Roden et al. | |

(Continued)

FOREIGN PATENT DOCUMENTS

| | | |
|---|---|---|
| DE | 10003782 A1 | 12/2001 |
| WO | 2014066654 A1 | 5/2014 |

(Continued)

OTHER PUBLICATIONS

Extended European Search Report issued in counterpart application No. EP18151021.5, dated Jul. 16, 2018 (8 pages).

*Primary Examiner* — Son T Le

(57) ABSTRACT

A sensing system for obtaining a gradient of soil properties in real-time as a function of soil depth is disclosed herein. The sensing system includes a support structure coupled to an agricultural implement and which is rotatable about a rotational axis relative to a frame of the agricultural implement. A sensor is arranged on a surface of the support structure and configured to generate an output signal indicative of the measured soil property based on a sensed a capacitance change corresponding to a change in a dielectric property of a measured soil sample with which the sensor interacts. A measuring unit is coupled to the at least one sensor and processes the output signal generated by the at least one sensor to generate a gradient profile of the soil properties in real-time as a function of one or more depths for display on a user interface.

13 Claims, 6 Drawing Sheets

(51) Int. Cl.
*G01S 19/13* (2010.01)
*A01C 21/00* (2006.01)
*A01B 47/00* (2006.01)
*A01B 79/00* (2006.01)
*A01C 5/06* (2006.01)

(56) References Cited

U.S. PATENT DOCUMENTS

| | | | |
|---|---|---|---|
| 2008/0199359 A1* | 8/2008 | Davis | G01D 5/2405 422/82.01 |
| 2013/0112122 A1* | 5/2013 | Blomme | A01C 5/062 111/149 |
| 2013/0250305 A1 | 9/2013 | Holland | |
| 2014/0303854 A1 | 10/2014 | Zielke | |
| 2016/0169413 A1 | 6/2016 | Camacho et al. | |
| 2018/0184581 A1* | 7/2018 | Morgan | G01N 21/4738 |

FOREIGN PATENT DOCUMENTS

| | | |
|---|---|---|
| WO | 2014153157 A1 | 9/2014 |
| WO | 2014186810 A1 | 11/2014 |
| WO | 2015171908 A1 | 11/2015 |
| WO | 2016205422 A1 | 12/2016 |

* cited by examiner

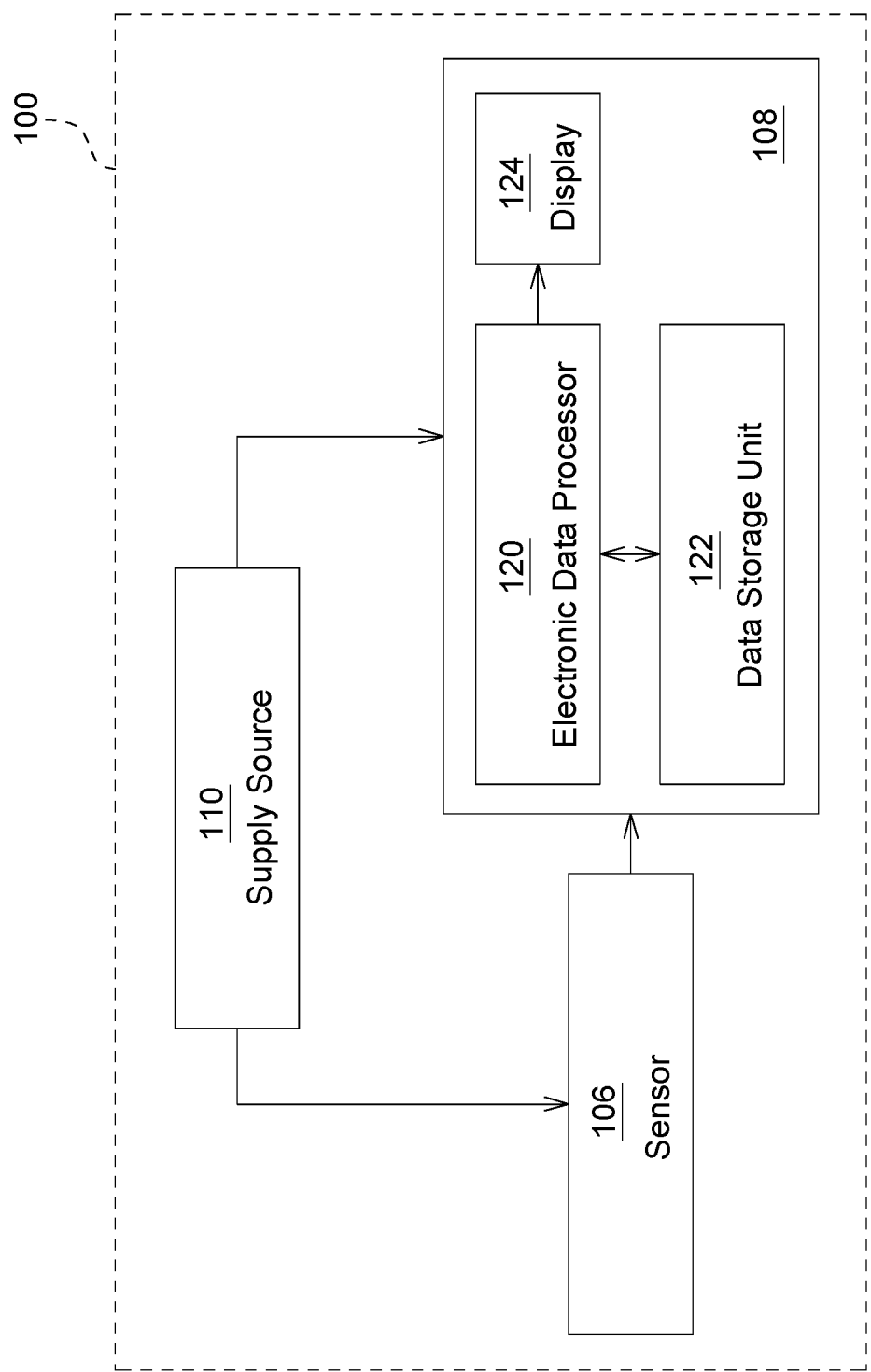

SENSING SYSTEM FOR MEASURING SOIL PROPERTIES IN REAL TIME

TECHNICAL FIELD

The present disclosure generally relates to a sensing system that utilizes real-time data measurements to obtain gradient profiles of soil properties.

BACKGROUND

In farming applications, it is often desirable to know certain properties of the soil in real-time as the farmer is performing a task such as planting or tilling. Such properties may include moisture, compaction, temperature, and trench depth; each of which can be of extreme importance in ensuring optimal yields. For example, inadequate moisture or temperature conditions may adversely affect crop production, thereby leading to decreased yields.

Drawbacks to some prior art approaches, however, include increased costs or decreased sensor resolution. As such, there is a need in the art for a sensor system that provides increased resolution at lower costs.

SUMMARY

In accordance with one embodiment, a sensing system for obtaining a gradient of soil properties in real-time as a function of soil depth is provided. The sensing system includes a support structure that is coupled to an agricultural implement and is rotatable about a rotational axis relative to a frame of the agricultural implement. The support structure is adapted for ground engagement and a sensor is arranged on a surface of the support structure. The sensor is configured to sense a change in capacitance corresponding to a change in dielectric property of a measured soil sample with which the sensor interacts, and is configured to generate an output signal indicative of the measured soil property. A measuring unit is coupled to the at least one sensor and configured to process the output signal generated by the at least one sensor and generate a gradient profile of the soil properties in real-time as a function of one or more depths for display on a user interface.

BRIEF DESCRIPTION OF THE DRAWINGS

FIG. 1 is a block diagram of a sensor system according to an embodiment;

Like reference numerals are used to indicate like elements throughout the several figures.

DETAILED DESCRIPTION

Figure 2A:
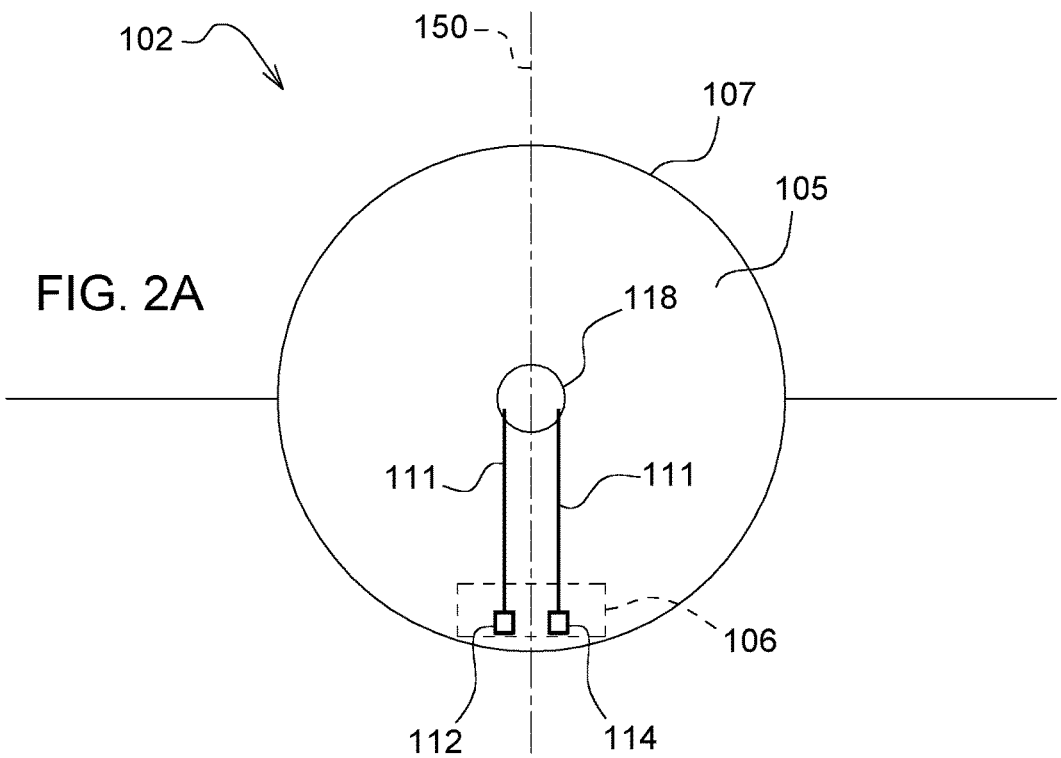
FIG. 2A is a front view of a sensor incorporated in the sensor system of FIG. 1 according to an embodiment.
Figure 2B:
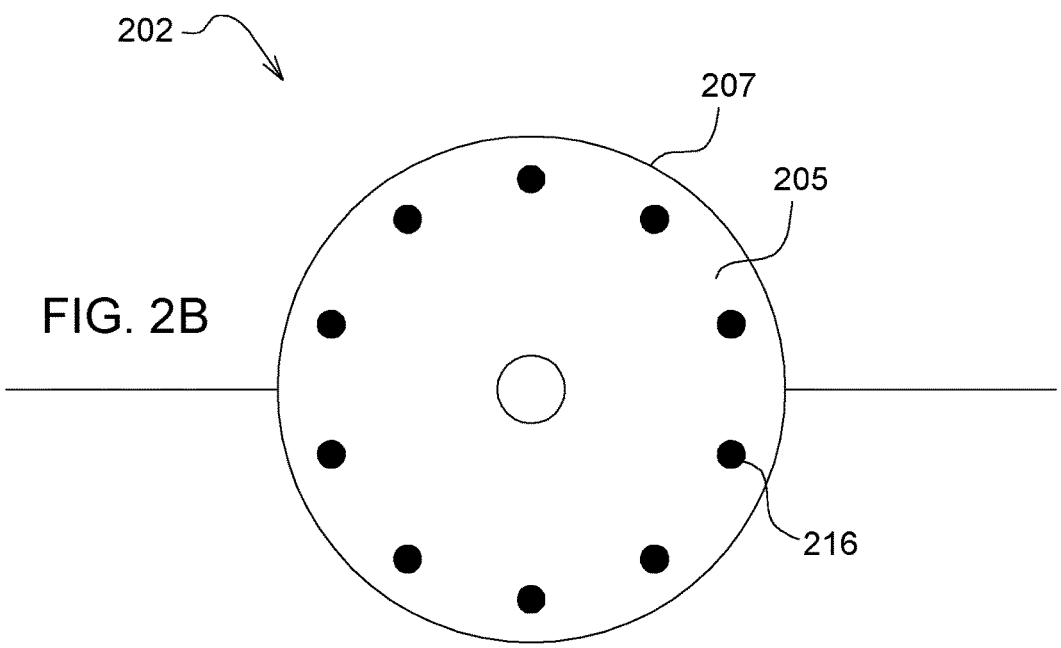
FIG. 2B is a front view of a sensor incorporated in the sensor system of FIG. 1 according to an embodiment.
Figure 4A:
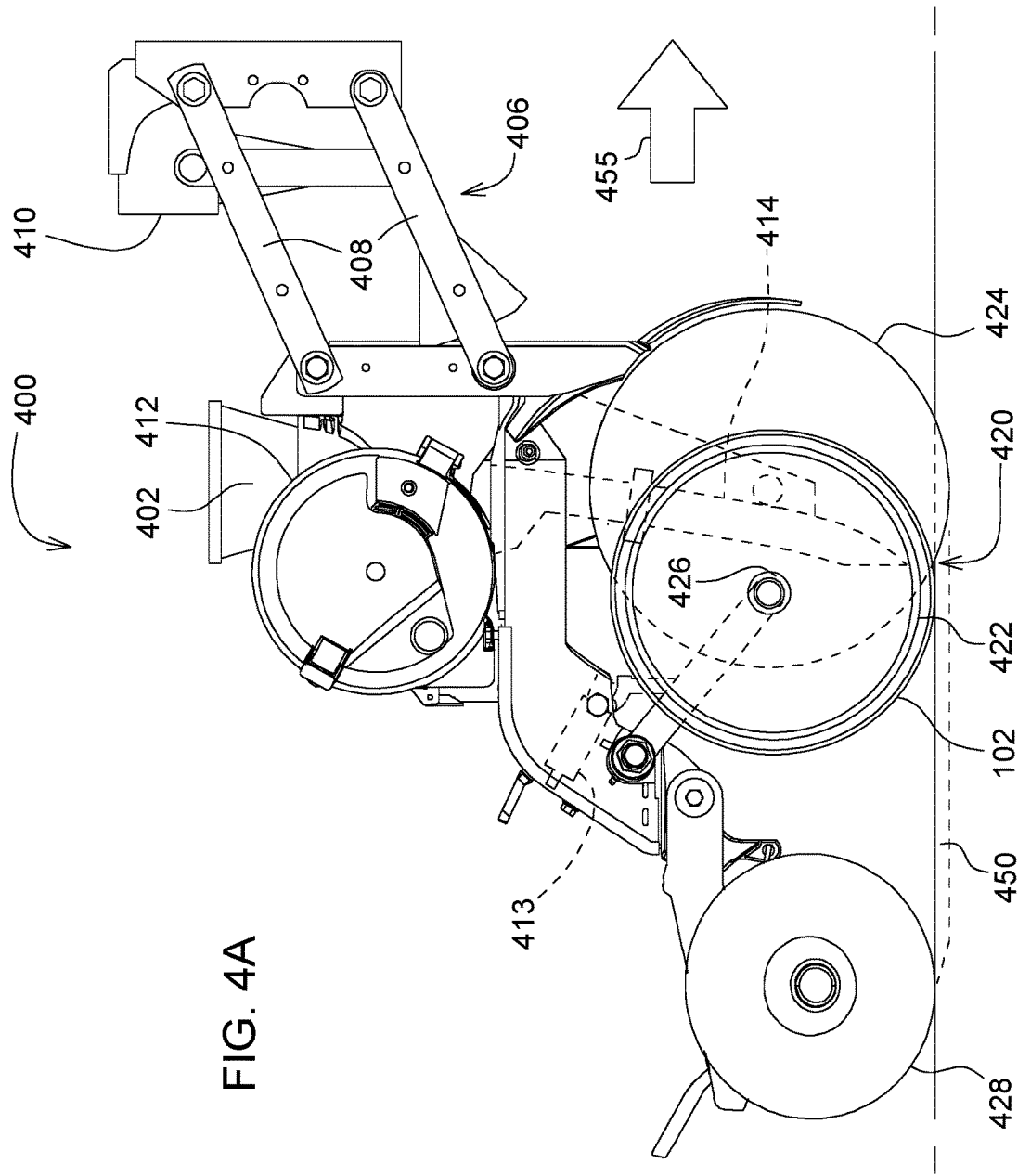
FIG. 4A is a side view of a planter unit in which the sensor system of FIG. 1 is incorporated according to an embodiment.
Figure 4B:
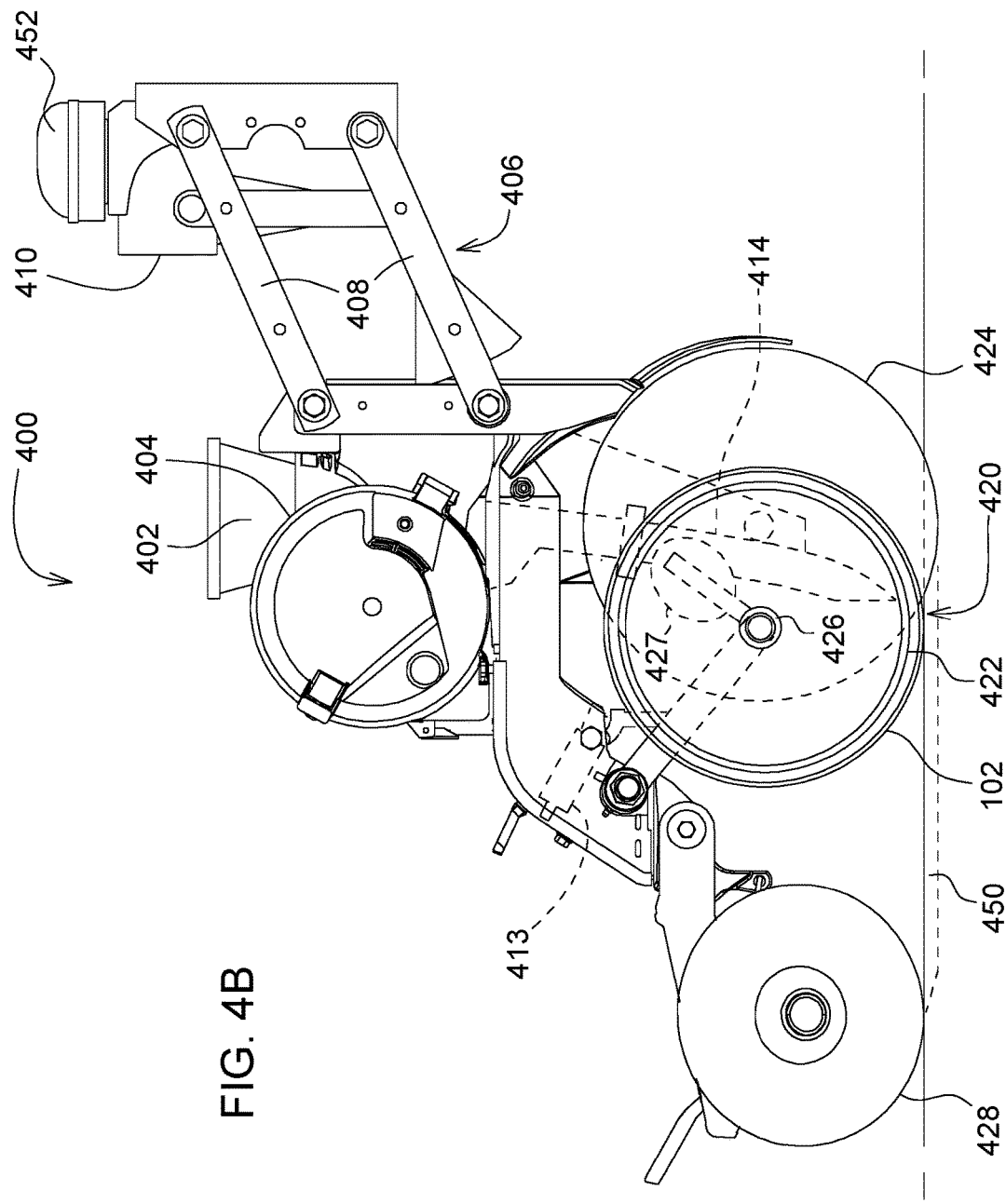
FIG. 4B is a side view of a planter unit in which the sensor system of FIG. 1 is incorporated according to an embodiment.

For purposes of clarity, the present disclosure will be described as being implemented in a planter unit. It should be noted, however, that the present disclosure may also be employed in a variety of planting and/or soil preparation applications to include, but not limited to, tillage, seeding, and others. Referring to FIGS. 1-2B, a sensing system 100 for determining soil properties in real time is shown according to an embodiment. In embodiments, the sensing system 100 can comprise at least one sensor 106 disposed on a support structure 102 (in FIG. 2A) and operatively coupled to a measuring unit 108. The support structure 102 can be adapted for coupling to an agricultural implement (e.g., planter unit 400 in FIG. 4A) and arranged such that it rotationally engages with or penetrates the surrounding soil as the implement is moved throughout a field. In some embodiments, the support structure 102 can comprise a disc or another wheel-like structure (refer, e.g., to FIG. 2A) that comprises at least one aperture 118 formed therein for receiving an axle shaft 426 or bearing of the agricultural implement. In some embodiments, the support structure 102 may be coaxially aligned with the at least one opener disc 422 (see FIG. 4A and FIG. 4B) along the rotational axis 424 of the axle 426. In other embodiments, the support structure 102 may include an opener disc such as opener disc 422 with the sensor 106 being arranged on an outer surface of the opener disc. In still other embodiments, the support structure 102 can be rotationally or fixedly coupled to a second axle (not shown) and arranged following the opener disc 422.

The at least one sensor 106 can be arranged proximate an outer periphery 107 (in FIG. 2A) of the support structure 102 on a sensing surface 105 to provide the sensor 106 with increased soil interaction as measurements are taken. In some embodiments, the sensor 106 can be configured as a capacitive sensor that is responsive to capacitance changes related to changes in the dielectric properties of the surrounding soil as the sensor 106 interacts with the soil. For example, the sensor 106 can comprise a first conductive element 112 spaced apart from a second conductive element 114 by a predetermined distance such that each is arranged generally offset from a center axis 150 of the support structure 102 so as to form a capacitor. The first and second conductive elements 112, 114 can comprise a metallic material such as gold, nickel, aluminum, copper, alloys, combinations thereof, or any other suitable electrical current carrying materials. A supply source 110, which may include, for example, a harvested energy source or an AC or DC power source, is electrically coupled to sensor 106 via leads 111. The supply source 110 transmits a supply signal (e.g., an alternating or pulsed electrical signal) to at least one of the first or second conductive elements to generate an electric field proximate the conductive elements 112, 114, which can be influenced by the dielectric property of the soil. For example, the dielectric property of the soil may change depending upon the depth from the surface of the soil or the geographic location from which the sensor measurement of the sensor 106 is taken. For example, as the sensor 106 interacts with soil, soil samples having uniform or variable dielectric properties will pass through the spaced region of the first and second conductive element 112, 114 thereby distorting the electric field and resulting in a change in the capacitance. This resulting change in capacitance is measured by the measuring unit 108.

As depicted, the measuring unit 108, which is also powered by supply source 110 or a suitable direct current source, can be configured to receive and process data signals outputted by the sensor 106 related to the various soil properties (e.g., soil moisture, density, temperature, ion mobility, pH levels, depth, etc.) based upon the measured capacitance or other measured soil property. In some embodiments, the measuring unit 108 can comprise a portable communications and/or computing device mounted inside a cab of an operator's vehicle (e.g., a tractor) to which the implement is attached. In other embodiments, the measuring unit 108 may be located remotely at a remote data processing facility as will be discussed with reference to FIG. 3. The measuring unit 108 may include an electronic data processor 120, a data storage unit 122 coupled to the processor 120, and a display 124 for displaying data processed by processor 120. Processor 120 may include a microprocessor, a microcontroller, a digital signal processor, a programmable logic controller, or other suitable computing devices capable of processing sensor data in real time. For example, the processor 120 may determine a dielectric property of the soil based on the measured capacitance and generate a gradient profile of the soil properties for one or more corresponding soil depths below a surface of the soil for display on display 124 (e.g., as a map of soil property versus position in a field) to allow an operator to view such information in real time. In other embodiments, the processed sensor data may be stored in memory 122, which may include, but is not limited to, random access memory (RAM), read only memory (ROM), optical data storage, dynamic data storage, and/or combinations thereof. For example, in some embodiments, the processor 120 may retrieve data stored in memory 122 to allow an operator to use such data for diagnostic, calibration or historical purposes.

With respect to FIGS. 1-2B, it will be appreciated by those skilled in the art that FIGS. 1-2B are not drawn to scale and are for illustrative purposes only. Notably, the size, dimensions, structural layout, and quantity of the various components can and will vary in other embodiments. For example, in some embodiments, the support structure, such as support structure 202, can comprise a plurality of protruding elements 216 arranged to equidistantly extend around the sensing surface 205 of the support structure 202 proximate the outer periphery 207 to facilitate preparation of the soil as the implement is moved throughout a field as illustrated in FIG. 2B. In other embodiments, sensing system 100 may comprise a plurality of sensors 106 axially aligned along the center axis 150 or arranged on each of the protruding elements 216 or at least two rows of sensors 106 concentrically arranged on support structure 102 about its rotational axis or central aperture 118. In still other embodiments, sensing system 100 may further comprise one or more secondary sensors, such as temperature sensors to allow simultaneous monitoring of temperature and other related soil properties.

Figure 3:
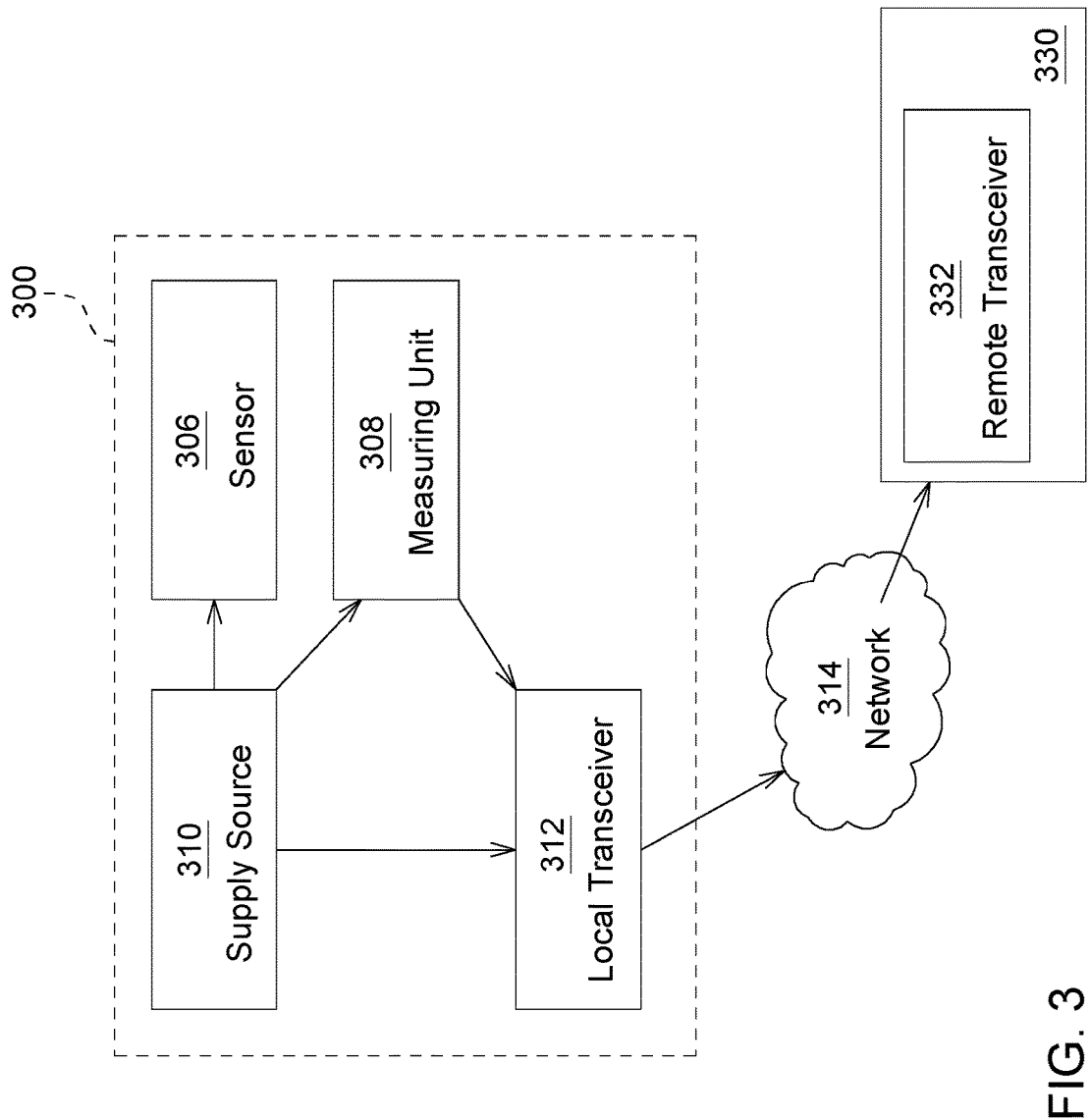
FIG. 3 is a block diagram of a sensor system according to an embodiment

Referring now to FIG. 3, a sensing system 300 is shown, which is substantially similar to sensing system 100 discussed with reference to FIG. 1. In embodiments, sensing system 300 may comprise a supply source 310 electrically coupled to a sensor 306, measuring unit 308, and a local transceiver 312. The local transceiver 312 may be configured to transmit and receive data transmissions to and from one or more remote transceivers 332 wirelessly over network 314, which may include the Internet. For example, as illustrated, the local transceiver 312 can transmit sensor data from measuring unit 308 to a remote processing unit 330 having a remote transceiver 332. The transceivers 312, 332 may be compatible with IEEE 802.11 and/or Bluetooth protocols and access to network 314 may be provided, for example, via a local area network (LAN), wide area network (WAN), wireless area network (WLAN), or suitable communication network. In some embodiments, the remote processing unit 330 can perform the functions described above with respect to the measuring unit 108. In other embodiments, the remote processing unit 330 may be configured to perform additional processing or data analysis, which may be made available to a secondary user or operator.

In FIG. 4, a planter unit 400 in which sensor 106 is incorporated is shown according to an embodiment. The planter unit 400 can comprise a hopper 402 arranged in a generally upright position that is mounted to a frame 404. A parallel arm arrangement 406 comprising linkages 408 and an actuation device 410 can be mounted to frame 404 in a cantilever-like configuration such that it extends outwardly and away from frame 404. In some embodiments, actuation device 410 can be coupled to at least one of linkages 408 and can include mechanical, pneumatic, hydraulic, or other suitable actuators to apply lift and/or downforce to planter unit 400. A metering unit 412 having a generally circular configuration can be arranged beneath hopper 402 and can be configured to distribute seeds received from hopper 402 into a seed tube 414. The seed tube 414 directs the seeds received from the metering unit 412 to a soil opening 450 formed in the ground by an opener assembly 420.

The opener assembly 420 can comprise at least one opener disc 422 that is arranged to create the soil opening 450 for receiving seeds or other materials at a predetermined depth upon engagement with the soil. In some embodiments, support structure 102, as discussed with reference to FIG. 1, may be coaxially aligned with the at least one opener disc 422 along the rotational axis 424 of the axle 426. At least two gauge wheels 424 are mounted proximate opener assembly 420 such that the soil penetration depth of the opener disc 422 and support structure 102 are regulated by gauge wheels 424. For example, as previously discussed, actuation device 410 operates to apply a downforce to planter unit 400, which in turn applies applicable downforces to each of the ground engaging devices (i.e., gauge wheels 424, opener disc 422, and support structure 102) mounted to planter unit 400. Once the devices are lowered, a gauge wheel adjustment mechanism 413 enables the vertical position of the gauge wheels 424 to be adjusted relative to the opener disc 422 and support structure 102, which establishes the depth to which the opener disc 422 and support structure 102 are inserted into the soil (i.e., the depth of the soil opening 450). A closing wheel assembly 428 can be arranged following the opener assembly 420, support structure 102, and gauge wheels 424 and is operable to close the soil opening 450 formed by opener assembly 420. In other embodiments, referring now to FIG. 4B, planter unit 400 may further comprise a location-determining receiver 452, such as a satellite navigation receiver, that is mounted to the planter unit 400 and configured to provide field location data. For example, the location-determining receiver 452 can be used to determine the field location where each soil measurement is taken such that a 2-dimensional or 3-dimensional plot of the field location and corresponding soil property may be generated. In still other embodiments, planter unit 400 may also comprise a scraper unit 427 mechanically coupled to the axle shaft 426 that is configured to remove excess dirt or other residual buildup from support structure 102 and conductive elements 112, 114. For example, in muddy soil conditions, mud or other similar materials may stick to the support structure 102 and interfere with the sensing accuracy of sensor 106. Therefore, to prevent such interference, scraper unit 427 will operate to clear excess material from support structure 102 and conductive elements 112, 114 as they are rotated above the ground.

Figure 5:
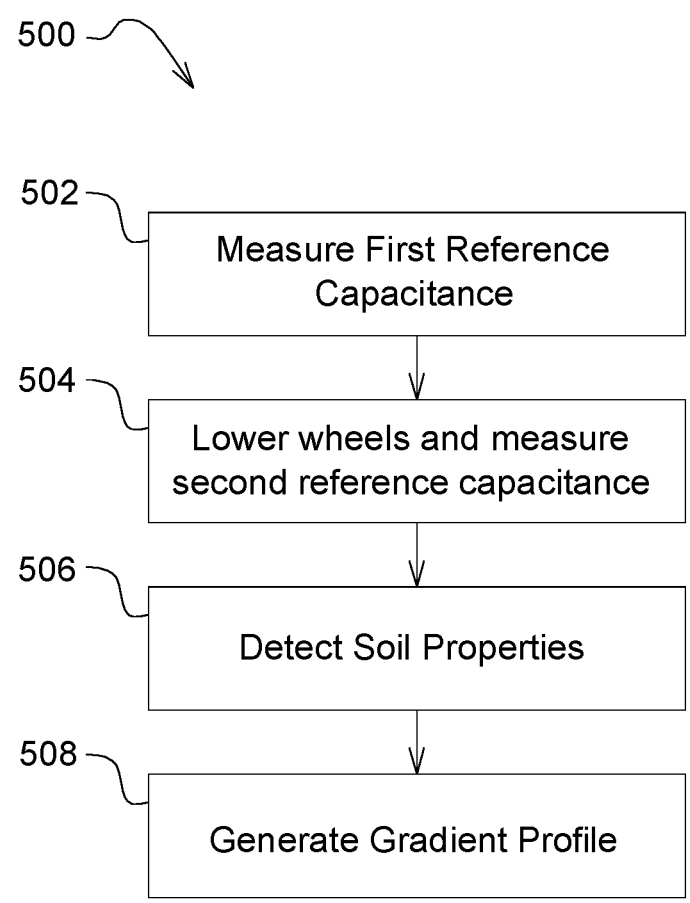
FIG. 5 is a flow diagram of a method for obtaining a gradient of soil properties utilizing the sensing system of FIG. 1.

In FIG. 5, a flow diagram of a method 500 for carrying out the present disclosure is shown. At 502, and prior to operation, a first reference capacitance may be measured while the sensor 106 is positioned above the ground and stored in memory 122. In other embodiments, however, the first reference capacitance may be measured and stored during manufacturing. Once the measurement is taken, at 504, an operator may input a command through a user interface of display 124 to enable adjustment of the vertical position (i.e., raising or lowering) of the gauge wheels 424, which, in turn, adjusts the vertical position of the opener disc 422 and the support structure 102 in which sensor 106 is arranged. This establishes the penetration depth to which the opener disc 422 and support structure 102 are inserted into the soil, i.e., the depth of the soil opening 450. Upon insertion, a second reference capacitance may be measured and stored in memory 122 while the planter unit 400 is in a rest state.

Once planter unit 400 is in operation and moving throughout a field, at 506, a plurality of capacitance measurements are taken by sensor 106 and transmitted to measuring unit 108. For example, as the support structure rotates throughout the soil, the plurality of capacitance measurements are taken above and beneath the soil and compared against the first and second reference capacitances to determine an overall change in capacitance of sensor 106. For example, because the difference in the dielectric constant between air (~1), soil (~3 to ~5) and water (~80) is quite large, it would be quite evident when the sensor 106 enters (i.e., dielectric change from air to soil) and exits the soil (i.e., dielectric change from soil to air) as the support structure 102 is rotating.

Next at 508, a gradient profile of the measured soil properties is generated. For example, measuring unit 108 processes the measured capacitances to determine corresponding soil properties (e.g., temperature, moisture content, density), which may be stored in memory 122 or plotted against the depth in a 2-dimensional curve on display 124 to generate the gradient. Notably, the displayed depth measurements, which may be determined in a number of ways, will include measurements taken from the soil's surface downward (i.e., measurements taken once the sensor enters the soil). For example, in some embodiments, sensing system 100 may further comprise an angle sensor (not shown) coupled to the axle shaft 426 that is used to determine the depth at which sensor 106 is positioned in the soil based on the angular position of support structure 102. In such a configuration, the angle sensor may be configured to generate sinusoidal output signals (i.e., cosine and sine signals) that are used to determine the angular position of the support structure 102. For example, measuring unit 108 can be configured to compute an arc tangent function utilizing the output signals to determine a corresponding rotation angle. In other embodiments, the rotational velocity of the support structure may be used to determine the depth. Additionally, in embodiments in which the support structure comprises the opener disc, the depth may be determined by sensing abrupt changes in impedance between the air and the soil along with the angular travel of the support structure.

Without in any way limiting the scope, interpretation, or application of the claims appearing below, a technical effect of one or more of the example embodiments disclosed herein is sensor system and method for obtaining a gradient of soil properties in real time. While the present disclosure has been illustrated and described in detail in the drawings and foregoing description, such illustration and description is not restrictive in character, it being understood that illustrative embodiment(s) have been shown and described and that all changes and modifications that come within the spirit of the present disclosure are desired to be protected. Alternative embodiments of the present disclosure may not include all of the features described yet still benefit from at least some of the advantages of such features. Those of ordinary skill in the art may devise their own implementations that incorporate one or more of the features of the present disclosure and fall within the spirit and scope of the appended claims.

What is claimed is:

1. A sensing system for obtaining a gradient of soil properties in real-time as a function of soil depth, the sensing system comprising:
   a support structure adapted for ground engagement and coupling to an agricultural implement, wherein the support structure is rotatable about a rotational axis relative to a frame of the agricultural implement;
   at least one sensor arranged on the support structure, wherein the at least one sensor is configured to sense changes in a capacitance corresponding to changes in a dielectric property of a measured soil sample with which the at least one sensor interacts, and wherein the at least one sensor is configured to generate an output signal indicative of the measured soil property; and
   a measuring unit coupled to the at least one sensor, wherein the measuring unit is configured to process the output signal generated by the at least one sensor and generate a gradient profile of the soil properties in real-time as a function of one or more corresponding depths from a surface of the soil of a field for display on a user interface.

2. The sensing system of claim 1, wherein the at least one sensor comprises two or more sensors arranged on the support structure.

3. The sensing system of claim 1, wherein the at least one sensor comprises at least two conductive elements equidistantly spaced apart from one another and offset from a center axis of the support structure.

4. The sensing system of claim 3, wherein the at least two conductive elements comprises one or more of a copper material, a gold material, a silver material, or combinations thereof.

5. The sensing system of claim 1, further comprising a secondary sensor selected from the group consisting of a temperature sensor, an angle sensor, or combinations thereof.

6. The sensing system of claim 1, wherein the support structure comprises a wheel structure having at least one aperture arranged therein.

7. The sensing system of claim 1, wherein the support structure comprises at least one or more opener discs of an opener assembly.

8. The sensing system of claim 1, wherein the support structure comprises a plurality of protruding elements arranged to extend around a sensing surface of the support structure proximate an outer periphery of the support structure so as to facilitate preparation of the measured soil sample, and wherein the at least one sensor comprises a plurality of sensors respectively arranged on each of the plurality of protruding elements.

9. The sensing system of claim 1, wherein the at least one sensor is arranged on a bottom surface of an outer periphery of the support structure.

10. The sensing system of claim 1, wherein the measured soil property comprises one or more of the following: soil moisture, soil density, soil temperature, ion mobility, soil pH levels.

11. The sensing system of claim 1 further including a satellite navigation receiver for determining each position of the at least one sensor and its associated respective measurements of the soil properties.

12. The sensing system of claim 11, wherein the satellite navigation receiver is adapted to determine a vertical height of the implement or the vehicle that is associated with each position of the at least one sensor and its associated respective measurements of the soil properties.

13. A method for generating a gradient of soil properties in real-time as a function of soil depth, the method comprising:
   providing at least one sensor arranged on a support structure, wherein the support structure is coupled to an agricultural implement and adapted for rotational engagement with the soil;
   sensing with the at least one sensor a capacitance change indicative of a changing dielectric property of the measured soil sample as the agricultural implement is moved throughout the field; and
   determining with a processor a dielectric property of the measured soil sample in real time to generate a gradient profile of the determined soil property as a function of depth.

* * * * *